United States Patent
Wilson, Jr.

(10) Patent No.: US 9,198,440 B2
(45) Date of Patent: Dec. 1, 2015

(54) HUMANE RODENT EUTHANASIA MACHINE

(71) Applicant: William Carroll Wilson, Jr., Clayton, DE (US)

(72) Inventor: William Carroll Wilson, Jr., Clayton, DE (US)

( * ) Notice: Subject to any disclaimer, the term of this patent is extended or adjusted under 35 U.S.C. 154(b) by 186 days.

(21) Appl. No.: 13/961,531

(22) Filed: Aug. 7, 2013

(65) Prior Publication Data

US 2015/0040892 A1    Feb. 12, 2015

(51) Int. Cl.
| | | |
|---|---|---|
| *A01K 1/03* | (2006.01) | |
| *A22B 3/00* | (2006.01) | |
| *A61D 7/04* | (2006.01) | |
| *A61M 11/02* | (2006.01) | |
| *A61M 11/06* | (2006.01) | |
| *A61M 16/01* | (2006.01) | |
| *A61M 16/18* | (2006.01) | |

(52) U.S. Cl.
CPC . *A22B 3/005* (2013.01); *A61D 7/04* (2013.01); *A61M 11/02* (2013.01); *A61M 11/06* (2013.01); *A61M 16/01* (2013.01); *A61M 16/18* (2013.01); *A61M 2202/0225* (2013.01); *A61M 2202/0241* (2013.01); *A61M 2250/00* (2013.01)

(58) Field of Classification Search
CPC ....... A22B 3/005; A61D 7/04; A61M 16/104; A61M 2202/0225; A61M 2202/0241
See application file for complete search history.

(56) References Cited

U.S. PATENT DOCUMENTS 7,549,397 B2 * 6/2009 Caplette ......................... 119/420
2006/0086038 A1 * 4/2006 Mosher ............................ 43/124

OTHER PUBLICATIONS

Valentine et al. Sedation or Inhalant Anesthesia before Euthanasia with CO2 Does Not Reduce Behavioral or Physiologic Signs of Pain and Stress in Mice. J. Am. Assoc. Lab. Anim. Sci., 51 (2012), pp. 50-57.*

* cited by examiner

*Primary Examiner* — Kristen Matter

(57) ABSTRACT

The present invention is a method for euthanizing animals humanely and painlessly by introducing droplets of liquid anesthesia into a chamber to cause the animal to become anesthetized. Carbon Dioxide is then introduced to induce a death to the animal that substantially meets or exceeds national and international standards for euthanasia.

23 Claims, 2 Drawing Sheets

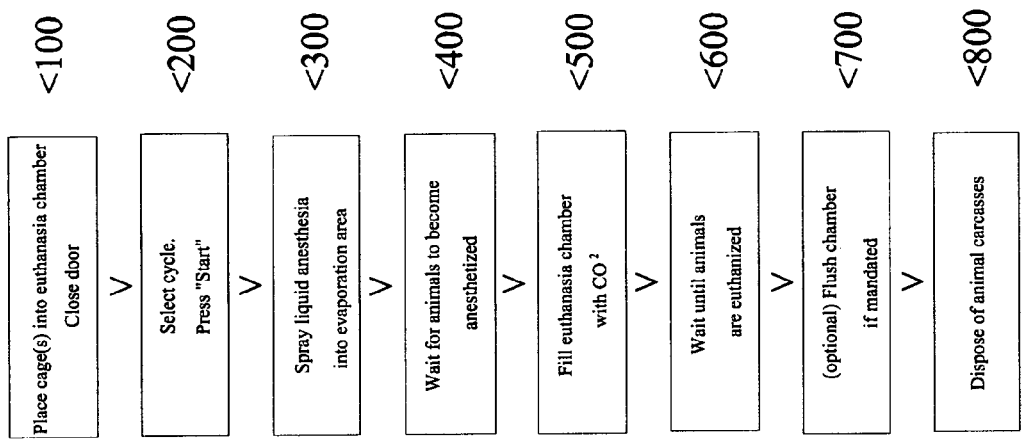

HUMANE RODENT EUTHANASIA MACHINE

BACKGROUND

1. Field of the Invention

The present invention relates generally to a method of humanely euthanizing animals.

2. Description of the Related Art

The subject of euthanasia in the biomedical research industry is not an easy one. Debates occur as to which are the preferred methods and reasons for euthanasia. New standards have been set by the Canadian Council on Animal Care (C.C.A.C.) requiring anesthesia before carbon dioxide. Debates continue within the industry and compliance to the new regulation may require more strict-enforcement.

Various methods for euthanizing animals are known in the art, including, for example, physical methods in the form of stunning, cervical dislocation, electrocution, pithing, decapitation, shooting, maceration, microwave radiation and exsanguinations. One may also use non-inhalant pharmacological agents, inhalant anesthetics or non-anesthetic gases.

In determining the type of euthanizing process to use, individuals are urged to consider the humaneness and pain involved in the process, despite the inevitable demise of the animal. As such, a set of criteria have been set forth to be used when determining what process of euthanasia to use. The criteria include: (1) ability to induce loss of consciousness and death without causing pain, distress, anxiety, or apprehension; (2) time required to induce loss of consciousness; (3) reliability; (4) safety of personnel; (5) irreversibility; (6) compatibility with requirement and purpose; (7) Compatibility with subsequent evaluation, examination, or use of tissue; (8) drug availability and human abuse potential; (9) compatibility with species, age, and health status; (10) ability to maintain equipment in proper working order; and (11) safety for predators and scavengers should the carcass be consumed.

When considering the criteria, many experts find that on the whole, exposure of carbon dioxide gas to the animal is one of the more humane means euthanizing the animal. However, many research papers discussing this topic also identify a high level of distress that is prevalent with euthanasia using carbon dioxide alone, as a result of the tests Canada now requires the use of an anesthesia before the introduction of carbon dioxide.

Carbon dioxide is the preferred method of euthanizing small animals and rodents because it is a relatively inexpensive gas that is colorless and odorless at low concentrations. Carbon dioxide is also considered to be quickly and readily taken into the body. Narcotic effects of $CO_2$ are well known, but the burning of the eyes, lungs and nasal passages due to carbolic acid make it inhumane. By introducing an anesthetic to small animals such as Isoflurane before introducing carbon dioxide the animals are euthanized in the most humane way possible.

Presently, other euthanasia processes involving carbon dioxide gas as the means of euthanizing small animals such as rodents, have carbon dioxide introduced to cause death by suffocation. Such processes of introducing carbon dioxide that is not preceded by anesthesia tend to dramatically increase the stresses upon the animal and thereby make its impending death less humane and more painful. For example, studies have shown that too low of concentration of carbon dioxide is considered a potent respiratory stimulant resulting in a tenfold increase in the ventilation rate and a feeling of profound respiratory distress.

What is desired is a means of euthanizing one or more animals using liquid anesthetic such as Isoflurane to anesthetize the animals followed by carbon dioxide so as to substantially limit the physical stresses that are placed upon the one or more animals when conventionally euthanizing with only carbon dioxide.

SUMMARY

The various exemplary embodiments of the present invention includes an apparatus of euthanizing one or more animals. The apparatus is comprised of the steps of placing the one or more animals into a holding cage or cages, placing a lid onto the cage or cages, placing the cage or cages into the euthanasia chamber, closing the door of the euthanasia chamber so as to create a sealed environment, choosing and entering the desired cycle on the HMI, pressing "Start" to begin the cycle, engaging the locking mechanism, introducing a liquid anesthetic that evaporates into the anesthesia chamber at a ratio to produce an anesthetic state for the one or more animals, ceasing introduction of the anesthesia into the euthanasia chamber for a first wait period to ensure that the effects of the anesthesia are achieved for the one or more animals, introducing the carbon dioxide gas into the euthanasia chamber until the carbon dioxide gas accounts for approximately 100% of an internal atmosphere inside the euthanasia chamber, ceasing introduction of the carbon dioxide into the euthanasia chamber for a second wait period to ensure irreversible euthanasia of the one or more animals, (flushing the chamber with fresh air when required) and removing and disposing of carcasses of the one or more animals.

The various exemplary embodiments of the present invention further include an apparatus of euthanizing one or more animals. The apparatus comprises of placing the one or more animals into a holding cage(s), placing a lid on the cage(s), placing the cage(s) into the euthanasia chamber, wherein the chamber is sealed, wherein the chamber is equipped with a lock that engages during operation, wherein the operation is controlled by a Programmable Logic Controller (PLC), wherein the operator uses a touch screen (HMI) to interface and communicate with the controller (PLC), wherein the (PLC) controls the components used in the operation of the euthanasia system. The anesthesia chamber further comprises of three inlets and at least one exhaust outlet, wherein the anesthesia chamber is connected to a liquid anesthetic source and a carbon dioxide gas sources for holding a gas with a regulator for reducing the delivery rate and a valve for controlling duration of flow. Wherein a venturi vacuum pump located within the chamber with a with a valve that delivers the pressurized gas that creates vacuum and propels the liquid anesthesia to spray onto an evaporation area located within the anesthesia chamber; a valve then opens and introduces the regulated carbon dioxide gas from the pressurized carbon dioxide gas sources into the euthanasia chamber for a predetermined flow period of time. After placing the one or more animals into the holding cages with lids and the cages are placed into the euthanizing chamber the door is closed and the cycle is selected, the operator enters "Start" to activate the program stored in the (PLC) and (HMI), the door locks, a liquid anesthetic is introduced into an evaporation area at a rate and ratio that produces an anesthetic state of the one or more animals, than the carbon dioxide gas is introduced into the euthanasia chamber until the carbon dioxide gas accounts for approximately 100% of an internal atmosphere inside the euthanasia chamber. The introduction of the carbon dioxide gas is ceased followed by a wait period to ensure irreversible euthanasia of the one or more animals. If the volume of carbon dioxide gas exceeds safety levels it will be flushed of carbon dioxide gas using a fan, vacuum or, compressed air. Finally, the euthanized animal(s) are removed from the holding cage(s) and disposed of.

BRIEF DESCRIPTION OF DRAWING

FIG. 2 Shows a flowchart of how the animals are processed using the euthanasia machine.

SPECIFICATIONS

Figure 1:
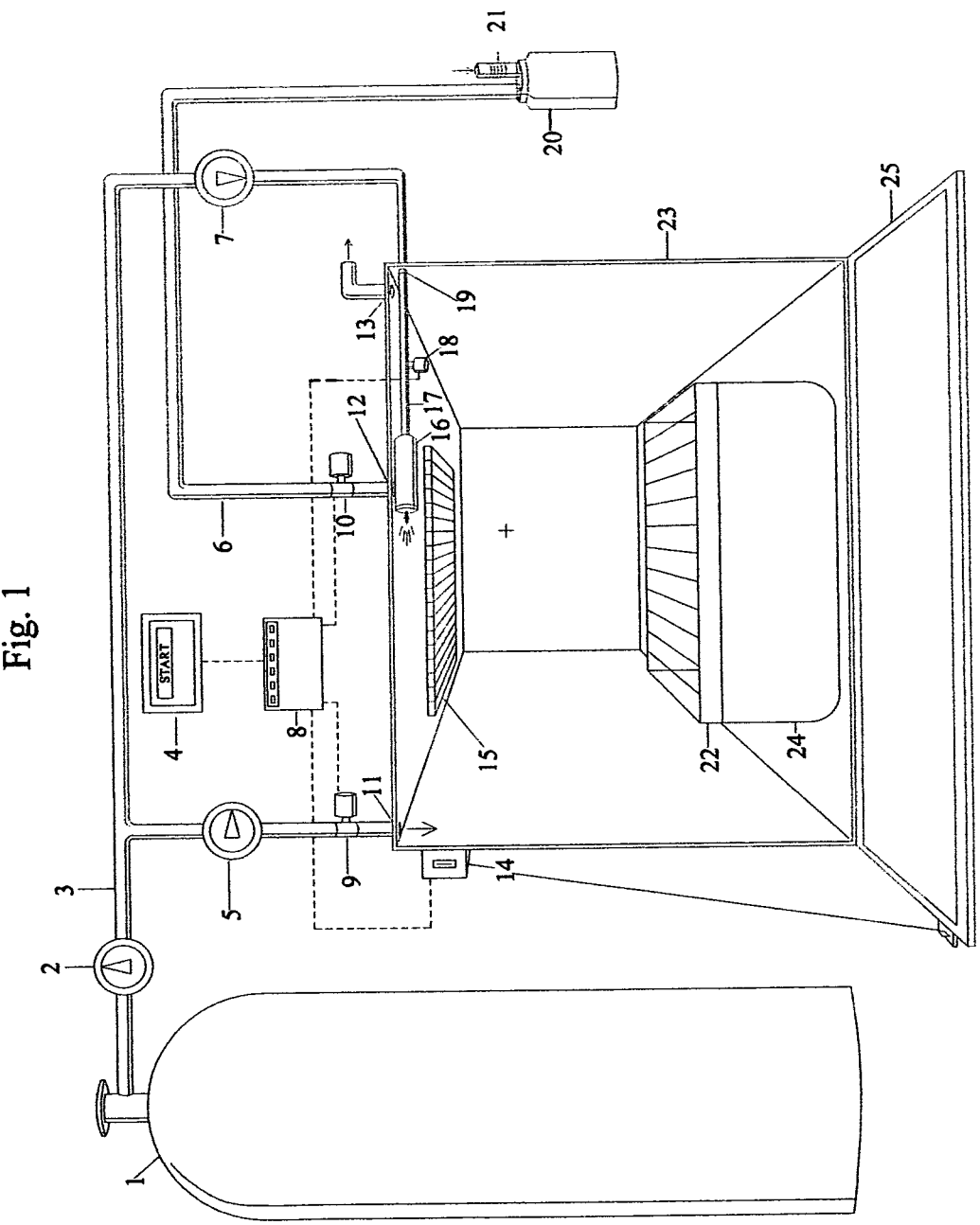
FIG. 1 Shows an example of an animal euthanasia machine.

The various exemplary embodiments of the present invention, which will become more apparent as the description proceeds, are described in the following detailed description in conjunction with the accompanying drawings, in which:

FIG. 1 is an illustrated representation of an exemplary embodiment of the present invention comprising a compressed $CO_2$ (carbon dioxide) tank (1), carbon dioxide (system) regulator (2), carbon dioxide supply line (3), Human Machine Interface (HMI) (4), carbon dioxide euthanasia chamber regulator (5), liquid anesthesia supply line (6), carbon dioxide regulator for venturi vacuum pump (7), Programmable Logic Controller (PLC) (8), carbon dioxide control valve to euthanasia chamber (9), liquid anesthesia valve (10), carbon dioxide inlet to euthanasia chamber (11), liquid anesthesia line inlet (12), outlet to exhaust system (13), locking mechanism (14), evaporation plate (15), venturi vacuum pump (16), carbon dioxide supply line for venturi pump (17), carbon dioxide control valve to venturi vacuum pump (18), carbon dioxide inlet to venturi vacuum pump (19), liquid anesthesia container (20), liquid anesthesia check valve (21), holding cage lid (22), euthanasia chamber (23), holding cage (24), door (25).

FIG. 2 is a flowchart of an exemplary embodiment of the present invention. The various exemplary embodiments of the present invention include a method and an apparatus for humanely and substantially painlessly euthanizing one or more animals. The method and apparatus are preferably utilized in a laboratory or veterinarian's setting with personnel trained at euthanizing animals. These embodiments will become more apparent in the follow description and related drawings: FIG. 1 and FIG. 2.

The various exemplary embodiments of the present invention include a method and apparatus of euthanizing one or more animals. The method is comprised of the steps of placing the one or more animals into a holding cage or cages (24), placing a lid onto the cage or cages (22), placing the cage or cages into the euthanasia chamber (23), closing the door (25), to seal the chamber (23), selecting the desired cycle and pressing "Start" on the (HMI) (4), to activate the (PLC) (8) that controls the various system components that perform the cycle, activating a locking mechanism (14), spraying a liquid anesthetic using a venturi vacuum pump (16) that is propelled by a compressed carbon dioxide source (1) that is regulated (2),(7) that travels via a carbon dioxide gas supply line (3) that enters the chamber through an inlet (19) and is metered by a valve for the carbon dioxide (18) and a valve for the liquid anesthesia (10) the liquid anesthesia source (20) is equipped with a check valve (21) that allows air to enter the container while preventing anesthesia from escaping the container, the liquid travels via a liquid supply line (6) through an inlet (12) into the euthanasia chamber (23) the liquid anesthesia is metered using a valve (10) and travels through the venturi vacuum pump (16) onto an evaporation area (15) within the euthanasia chamber (23) until an anesthetic state of the one or more animals is achieved, ceasing introduction of the liquid anesthetic into the euthanasia chamber (23) for a first wait period to ensure the effects of the anesthetic gas overtake the one or more animals, introducing the carbon dioxide gas from the carbon dioxide source (1) that is regulated (2), (5) that enters the euthanasia chamber through an inlet (11) that is metered by a valve (9) into the euthanasia chamber, displacing and replacing the anesthetic vapor, until the carbon dioxide gas accounts for approximately 100% of an internal atmosphere inside the euthanasia chamber, ceasing introduction of the carbon dioxide gas into the euthanasia chamber for a second wait period to ensure irreversible euthanasia of the one or more animals, (flushing the euthanasia chamber with fresh air if necessary) and removing and disposing of carcasses of the one or more animal The exemplary embodiments of the present invention can be used with cages of various sizes and constructions. In an exemplary embodiment described more in depth below, the cage in which the one or more animals is euthanized is comprised of plastic, however, the cage (24) can also be of wire or mesh construction and then covered with a lid (22) to ensure that the animals remain in the cage during the process.

No matter the composition of the cage material, a typical cage comprises a floor and four upstanding walls to form a generally rectangular surrounding. The cage may also comprise a top lid or cover (22) for enclosing the cage.

The present invention is designed to enable the laboratory personnel to efficiently and effectively attend to the euthanasia of the laboratory animals at the conclusion of the tests or experimental procedures. The method and apparatus of the present invention enables the animals to be euthanized painlessly and humanely without removing the animals from the cages in which the procedures were last performed. Thus, the animals need not be handled by the laboratory technicians. To this end, the apparatus of the present invention incorporates a sealed chamber (23) to place the cage(s) into, and a means to supply a liquid anesthesia (1),(2),(3),(6),(7),(10), (12), (16), (17), (18),(19), (20) and (21), an area for the anesthesia to evaporate (15) a means to supply carbon dioxide as a lethal gas (1), (2), (3),(5),(9),(11) to suffocate the animal(s) in an efficient and effective manner. In particular embodiment, the apparatus incorporates several control means (4), and (8), which enables the introduction of the proper quantity of anesthetic liquid and of lethal gas (carbon dioxide) into the euthanasia chamber, without the need for highly skilled supervision of this procedure.

The various exemplary embodiments include at least one carbon dioxide gas source (1) such as, for example, one or more research or medical, grade carbon dioxide pressurized containers (1). It is preferred that the carbon dioxide gas source have a pressure range of approximately 50 pounds per square inch (PSI) to approximately 150 PSI.

The carbon dioxide gas pressurized containers (1) are preferably connected to 3 regulator (2),(5) and (7). In a preferred embodiment, the regulator regulates the carbon dioxide, gas pressure at approximately 15 to 60 PSI.

Connected to the regulators (5) and (7) are valves (9) and (10) that meters the delivery of carbon dioxide. These valves can be controlled manually, electronically or pneumatically.

Although FIG. 1 is a graphic representation of an exemplary embodiment comprising of a carbon dioxide source (1) 3 regulators (2),(5) and (7), carbon dioxide supply line (3) liquid anesthesia line (6) control valves (9), (10) and (18), inlets (11), (12) and (19), liquid anesthesia supply container (20), check valve (21) an evaporation area (15) a holding cage (24) with a lid (22) an exhaust outlet (13). The function of the apparatus can be performed automatically using a Programmable Logic Controller (8) with a Human Machine interface (4) but can also be done manually, pneumatically or by using other electronic devices such as a personal computer, electronic timer, or Arduino module.

The anesthesia metering valve (18) and the carbon dioxide valves (9) and (10) may be connected to a control means. The control means such as but not limited to a Programmable Logic Controller may be programmed to open the anesthesia metering valve (10) for the liquid anesthesia and the carbon dioxide valves (9),(18) to open at one or more particular predetermined times, for a predetermined amount of time and at a predetermined flow rate of liquid anesthesia or gas.

When the valve (18) that supplies carbon dioxide gas to propel and spray the liquid anesthesia opens, the valve (10) that meters the amount of liquid anesthesia will open simultaneously, allowing the liquid to travel via the anesthesia supply line (6) After the predetermined amount of liquid anesthesia is sprayed onto the evaporation area both valves will close.

When the carbon dioxide valve (9) opens to supply the carbon dioxide via the gas supply line (3) of the present apparatus, carbon dioxide gas enters the euthanasia chamber through the carbon dioxide inlet. (11)

The carbon dioxide gas ($CO_2$), being a gas heavier than oxygen ($O_2$) and nitrogen ($N_2$), the other two main chemicals in safe and breathable air, settles to the bottom part of the cage, that is, closer to the floor. As the carbon dioxide gas fills the bottom part of the cage, the anesthetic particulates mixed with safe and breathable air is displaced up and out the exhaust outlet (13).

Normally, carbon dioxide gas is not a dangerous gas and typically comprises approximately 0.1% of breathable air. However, in high concentrations, the carbon dioxide gas can anesthetize a mammal and eventually asphyxiate it. If the volume of carbon dioxide gas exceeds safety limits a fan or compressed air supply can be used in conjunction with this apparatus to flush the anesthesia chamber.

In the various exemplary embodiments of the present invention shown in FIG. 2, one or more animals are placed in a cage or cages with lids. The cage or cages are placed in the euthanasia chamber. The door is closed to create a sealed chamber. See step 100.

Select the desired cycle from the H.M.I. cycle select menu. Enter selection. Enter "Start". See step 200.

Liquid anesthesia is sprayed into the evaporation area until a predetermined dose has been achieved. The valves close when the proper dose has been administered. See step 300.

Next a predetermined first wait period occurs to ensure that the anesthetic set point of the one or more animals has been reached. See step 400.

Next, the carbon dioxide valve opens for a predetermined flow period of time and rate until the carbon dioxide level in the euthanasia chamber is 100% of the total volume. See step 500.

Finally, after the carbon dioxide stops, a second wait period occurs to ensure that non reversible euthanasia of the one or more animals occurs. See step 600.

(Optional) If mandated the chamber is flushed with room air using a vacuum, fan or, air compressor system. See step 700.

When the one or more animals have been euthanized, the one or more animals' carcasses can be properly disposed of. See step 800.

By anesthetizing the animals with liquid anesthesia and then euthanizing with Carbon Dioxide the animals do not thrash about and experience stresses often involved and observed when the animals are sacrificed using carbon dioxide exclusively. Thus, the animals humanely and painlessly overcome by the anesthesia, and then carbon dioxide is introduced to ensure that the animals are humanely sacrificed.

If a mandate has been imposed requiring that the Carbon Dioxide be evacuated from the chamber the user would exercise the option of flushing the holding cage with a vacuum or air compressor.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

What is claimed is:

1. A method of euthanizing one or more animals comprising the steps of:
    placing the one or more animals into a holding cage, placing a lid onto the cage, placing the cage into a euthanizing chamber, and closing a chamber door wherein the euthanizing chamber is sealed;
    wherein the euthanizing chamber is connected to: a sprayable liquid anesthesia source and a valve to control a volume of liquid anesthesia that is sprayed, a compressed carbon dioxide gas source, at least one regulator to control a carbon dioxide gas flow rate, and at least one valve to control the duration of carbon dioxide flow into the euthanizing chamber;
    wherein the euthanizing chamber comprises: three inlets; at least one exhaust outlet connected to an exhaust vent or an activated charcoal filter; an anesthetic evaporation plate or evaporation chamber; and a venturi vacuum pump that is configured to spray the liquid anesthesia using the regulated compressed carbon dioxide gas to create a vacuum and propel the liquid anesthesia;
    wherein the euthanizing chamber houses one or more holding cages;
    spraying the liquid anesthesia into the euthanizing chamber using the venturi vacuum pump and onto the evaporation plate or into the evaporation chamber, followed by a first wait period to anesthetize the animals;
    after the first wait period is completed, opening the at least one valve to introduce regulated carbon dioxide gas from the compressed carbon dioxide gas source into the euthanizing chamber at a predetermined flow rate for a predetermined duration until the carbon dioxide gas displaces the liquid anesthesia and accounts for approximately 100% of an internal atmosphere inside the euthanizing chamber;
    ceasing introduction of the carbon dioxide gas into the euthanizing chamber for a second wait period to ensure irreversible euthanasia of the one or more animals;
    after the second wait period is completed, removing and disposing of carcasses of the one or more animals.

2. The method of claim 1, wherein the holding cage is equipped with a lid to prevent the one or more animals from escaping.

3. The method of claim 1, wherein the chamber door is large enough to allow the holding cage to be placed within the chamber.

4. The method of claim 1, wherein the euthanizing chamber comprises a Programmable Logic Controller (PLC) that provides signals to components used in the operation process.

5. The method of claim 1, wherein a Human Machine Interface (HMI) comprises a touch screen input that communicates with the Programmable Logic Controller (PLC).

6. The method of claim 1, wherein the euthanizing chamber comprises a locking mechanism that prevents the chamber door from opening during operation.

7. The method of claim 1, wherein the liquid anesthesia is sprayed onto the evaporation plate or into the evaporation chamber to allow the liquid to evaporate, thereby protecting the one or more animals from a direct mist.

8. The method of claim 1, wherein the at least one regulator to control the carbon dioxide gas flow rate comprises 3 regulators for reducing the pressure of carbon dioxide to an appropriate delivery rate.

9. The method of claim 1, wherein the at least one valve to control the duration of carbon dioxide flow into the euthanizing chamber comprises 2 valves.

10. The method of claim 1, wherein the compressed carbon dioxide gas source is a pressurized container.

11. The method of claim 1, wherein the liquid anesthesia source is a liquid stored in a container.

12. The method of claim 11, wherein the container is equipped with a check valve to prevent evaporation and allow the introduction of air.

13. The method of claim 1, wherein an anesthesia set point occurs when the internal atmosphere of the euthanasia chamber is sufficient to anesthetize the one or more animals.

14. The method of claim 1, wherein the one or more animals are birds or mammals comprising rodents.

15. The method of claim 1, wherein the first wait period is approximately 1 to approximately 5 minutes for the one or more animals to become anesthetized.

16. The method of claim 1, wherein the flow rate of carbon dioxide is approximately 5 liters per minute.

17. The method of claim 1, wherein the second wait period is approximately 2.5 to approximately 60 minutes for the one or more animals to suffocate.

18. The method of claim 1, wherein a fan, vacuum or compressed air is used to flush the carbon dioxide from the euthanizing chamber.

19. The method of claim 1, wherein a set point occurs when the internal atmosphere of the euthanizing chamber is sufficient to anesthetize the one or more animals, using approximately 2.5% to 4% saturation of Isoflurane.

20. The method of claim 1, wherein the liquid anesthesia is Isoflurane and the first wait period is 1 to 5 minutes for the one or more animals to become anesthetized.

21. The method of claim 1, wherein the flow rate of the carbon dioxide gas is approximately 5 liters per minute.

22. The method of claim 1, wherein the wait period is predetermined according to the age and species of the one or more animals.

23. An apparatus for humanely euthanizing one or more animals comprising:
a lockable euthanizing chamber comprising: three inlets; at least one exhaust outlet connected to an exhaust vent or an activated charcoal filter; an anesthetic evaporation plate or evaporation chamber; and a venturi vacuum pump that sprays a liquid anesthesia using regulated compressed carbon dioxide gas to create a vacuum and propel the liquid anesthesia within the euthanizing chamber;
wherein the euthanizing chamber is configured to house one or more lockable animal holding cages; and
wherein the euthanizing chamber is connected to: a sprayable liquid anesthesia source and a valve to control the volume of liquid anesthesia that is sprayed, a compressed carbon dioxide gas source, a regulator that controls a carbon dioxide gas flow rate, and a valve to control the duration of carbon dioxide flow into the euthanizing chamber.

* * * * *